United States Patent [19]

Hölscher et al.

[11] Patent Number: 5,710,138
[45] Date of Patent: Jan. 20, 1998

[54] BENZO[F]QUINOXALINEDIONE DERIVATIVES, THEIR PRODUCTION AND USE IN PHARMACEUTICAL AGENTS

[75] Inventors: Peter Hölscher; Lechoslaw Turski, both of Berlin, Germany

[73] Assignee: Schering Aktiengesellschaft, Berlin, Germany

[21] Appl. No.: 537,895

[22] PCT Filed: Apr. 28, 1994

[86] PCT No.: PCT/DE94/00495

§ 371 Date: Jan. 22, 1996

§ 102(e) Date: Jan. 22, 1996

[87] PCT Pub. No.: WO94/25470

PCT Pub. Date: Nov. 10, 1994

[30] Foreign Application Priority Data

Apr. 28, 1993 [DE] Germany .................... 43 14 592.2

[51] Int. Cl.⁶ .................... C07D 413/02; C07D 241/36; A61K 31/535; A61K 31/495
[52] U.S. Cl. .................... 514/80; 514/232.8; 514/250; 544/115; 544/337; 544/344
[58] Field of Search .................... 544/337, 344, 544/115; 514/250, 80, 232.8

[56] References Cited

U.S. PATENT DOCUMENTS 5,026,704  6/1991  Honore et al. .................... 514/250
5,081,123  1/1992  Honoré et al. .................... 514/250
5,559,106  9/1996  Jacobsen et al. .................... 514/81

FOREIGN PATENT DOCUMENTS 0511152  10/1992  European Pat. Off. .
9113878   9/1991  WIPO .
9308173   4/1993  WIPO .

*Primary Examiner*—Matthew V. Grumbling
*Attorney, Agent, or Firm*—Millen, White, Zelano, & Branigan, P.C.

[57] ABSTRACT

Compounds of formula I

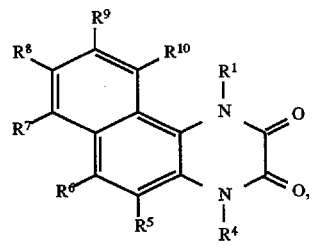

are described, in which substituents $R^1$–$R^4$ have the meanings mentioned in the application as well as their production and use in pharmaceutical agents.

10 Claims, No Drawings

BENZO[F]QUINOXALINEDIONE DERIVATIVES, THEIR PRODUCTION AND USE IN PHARMACEUTICAL AGENTS

This is a 371 of PCT/DE94/00495, filed Apr. 28, 1994.

The invention relates to benzo[f]quinoxalinedione derivatives, their production and use in pharmaceutical agents.

It is known that quinoxaline derivatives have an affinity to the quisqualate receptors and, because of this receptor binding, are suitable as pharmaceutical agents for the treatment of diseases of the central nervous system.

The compounds according to the invention have formula I

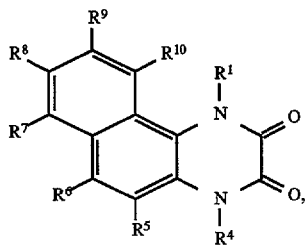

in which $R^1$ and $R^4$ are the same or different and mean hydrogen, $C_{1-12}$ alkyl substituted with $R^2$, $C_{2-12}$ alkenyl substituted with $R^2$, $C_{2-12}$ alkynyl substituted with $R^2$, $C_{3-7}$ cycloalkyl substituted with $R^2$, —$(CH_2)_n$—$C_{6-12}$ aryl, which is substituted with $R^2$ in the aryl or in the alkyl radical or —$(CH_2)_n$-hetaryl, which is substituted with $R^2$ in the hetaryl or alkyl radical, and $R^1$ and $R^4$ do not mean hydrogen at the same time, $R^5$, $R^6$, $R^7$, $R^8$, $R^9$ and $R^{10}$ are the same or different and mean hydrogen, halogen, nitro, $NR^{16}R^{17}$, $NHCOR^{11}$, $SO_{0-3}R^{12}$, $C_{3-7}$ cycloalkyloxy, $COR^{13}$, cyano, $CF_3$, $OCH_2CF_3$, $C_{1-6}$ alkyl or $C_{1-4}$ alkoxy, and $R^2$ is —CN, -tetrazole, —C(NOH)NH2, —CO—$R^3$ or —PO-XY and $R^2$ is the same or different in one to two places, and n is 0, 1, 2, 3, 4 or 5, $R^3$ means hydroxy, $C_{1-6}$ alkoxy or $NR^{14}R^{15}$, X and Y are the same or different and mean hydroxy, $C_{1-6}$ alkoxy, —O—$(CH_2)_p$—O—, $C_{1-4}$ alkyl or $NR^{14}R^{15}$ and p is 1, 2 or 3, and $R^{11}$ means $C_{1-6}$ alkyl or phenyl, which can be substituted with halogen, $R^{12}$ means hydrogen, $C_{1-4}$ alkyl, $NH_2$, $N(C_{1-4}$ alkyl$)_2$, —NH($C_{1-4}$ alkyl) —NH—$CH_2CONH_2$, —$CH_2CONH_2$, $CF_3$ or —NH—$(CH_2)_n$—$R^2$ and $R^{13}$ means hydroxy, $C_{1-6}$ alkoxy, $C_{1-6}$ alkyl or $NR^{14}R^{15}$, $R^{14}$ and $R^{15}$, $R^{16}$ and $R^{17}$ are the same or different and mean hydrogen, —CO—$C_{1-6}$ alkyl, phenyl or $C_{1-6}$ alkyl, which optionally can be substituted with $C_{1-4}$ alkoxy or with an amino group that is optionally mono- or disubstituted with $C_{1-4}$ alkyl, or together with the nitrogen atom can form a 5- to 7-membered saturated heterocycle, which can contain another N, S or O atom and can be substituted or can form an unsaturated 5-membered heterocycle, which can contain 1–3N atoms and can be substituted, as well as their isomers or salts, and, if $R^5$–$R^{10}$ is hydrogen, $R^1$ or $R^4$ does not mean methanephosphonic acid or ethane-1-phosphonic acid.

The compounds of general formula I also contain the possible tautomeric forms and comprise the E or Z isomers or, if a chiral center is present, the racemates or enantiomers.

The substituents are preferably in 6- and/or 7-position.

Substituent $R^2$ appears in one to two places, the same or different in any position on the alkyl, alkenyl, alkynyl, cycloalkyl, hetaryl, aryl or $(CH_2)_n$ radical.

Alkyl is to be understood to mean respectively a straight-chain or branched alkyl radical, such as, for example, methyl, ethyl, propyl, isopropyl, butyl, isobutyl, sec-butyl, pentyl, isopentyl, hexyl, heptyl, octyl, nonyl, decyl, and $C_{1-6}$ alkyl radicals are preferred.

Alkenyl especially comprises $C_{2-6}$ alkenyl radicals, which can be straight-chain or branched, such as, for example, 2-propenyl, 2-butenyl, 3-methyl-2-propenyl, 1-propenyl, 1-butenyl, vinyl.

Ethynyl, 1-propynyl, 2-propynyl, 1-butynyl with 2–4 carbon atoms are especially suitable as alkynyl radicals.

By $C_{3-7}$ cycloalkyl is meant respectively cyclopropyl, cyclobutyl, cyclopentyl, cyclohexyl and cycloheptyl, especially $C_{3-5}$ cycloalkyl.

As aryl radical, for example, phenyl, naphthyl, biphenyl and indenyl, especially $(CH_2)_n$-phenyl with n=0, 1 or 2, are mentioned.

As hetaryl radical, 5- or 6-membered heteroaromatic substances with 1–3 nitrogen atoms, such as, for example, pyrazole, imidazole, pyrazine, pyridine, pyrimidine, pyridazine, triazine, are suitable.

Halogen is to be understood to mean respectively fluorine, chlorine, bromine and iodine, especially fluorine, chlorine and bromine.

If $R^{14}$, $R^{15}$ and $R^{16}$, $R^{17}$ together with the nitrogen atom form a saturated heterocycle, then, for example, piperidine, pyrrolidine, morpholine, thiomorpholine, hexahydroazepine or piperazine are meant. As substituents of the heterocycle, $C_{1-4}$ alkyl groups can be mentioned, such as N-methyl-piperazine, 2,6-dimethylmorpholine or aryl groups such as phenylpiperazine. The substituent can appear in one to three places.

If $R^{14}$, $R^{15}$ and $R^{16}$, $R^{17}$ together with the nitrogen atom form an unsaturated heterocycle, then, for example, imidazole, pyrazole, pyrrole and triazole can be mentioned, which can be substituted in one to two places with cyano, $C_{1-4}$ alkyl, phenyl or $CO_2C_{1-6}$ alkyl.

Preferred are compounds with $R^2$ meaning —$COR^3$ or —POXY and $R^1/R^4$ meaning alkyl.

The physiologically compatible salts of organic and inorganic bases are suitable as salts, such as, for example, the readily soluble alkali and alkaline-earth salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, 1-amino-2, 3,4-butanetriol.

If a basic function is contained, the physiologically compatible salts of organic and inorganic acids are suitable, such as HCl, $H_2SO_4$, phosphoric acid, citric acid, tartaric acid, i.a.

The compounds of formula I as well as their physiologically compatible salts can be used as pharmaceutical agents because of their affinity to the AMPA or Kainat receptors. Because of their action profile, the compounds according to the invention are suitable for the treatment of diseases that are caused by hyperactivity of excitatory amino acids, such as, for example, glutamate or aspartate. Since the new compounds act as antagonists of excitatory amino acids and show a high specific affinity to the AMPA receptors, by displacing the radioactively-labeled specific agonist (RS)α-amino-3-hydroxy-5-methyl-4-isoxazolpropionate (AMPA) from the AMPA receptors, they are especially suitable for the treatment of those diseases that are affected by the receptors of excitatory amino acids, especially the AMPA receptor, such as for the treatment of neurological and psychiatric diseases. The neurological diseases that can be treated functionally and preventatively include, for example, neurodegenerative disorders, such as, Parkinson's disease, Alzheimer's disease, Huntington chorea, amyotrophic lateral sclerosis and olivopontocerebellar degeneration. According to the invention, the compounds can be used for the prevention of postischemic cell destruction, cell destruction after cerebral trauma, in the case of a stroke, hypoxia, anoxia and hypoglycemia and for the treatment of senile dementia, multiinfarct dementia as well as epilepsy and muscle spasms. The psychiatric diseases include anxiety conditions, schizophrenia, migraine, conditions of pain, as well as the treatment of sleep disorders or the withdrawal symptoms after drug abuse such as in the case of alcohol, cocaine, benzodiazepine or opiate withdrawal.

For use of the compounds according to the invention as pharmaceutical agents, the latter are brought into the form of a pharmaceutical preparation, which contains, besides the active ingredient for enteral or parenteral administration, suitable pharmaceutical, organic or inorganic inert vehicles, such as, for example, water, gelatin, gum arabic, lactose, starch, magnesium stearate, talc, vegetable oils, polyalkyleneglycols, etc. The pharmaceutical preparations can be in solid form, for example, as tablets, coated tablets, suppositories, capsules or in liquid form, for example, as solutions, suspensions or emulsions. Moreover, they optionally contain adjuvants such as preservatives, stabilizers, wetting agents or emulsifiers, salts for changing the osmotic pressure or buffers.

Especially suitable for parenteral use are injection solutions or suspensions, in particular aqueous solutions of the active compounds in polyhydroxyethoxylated castor oil.

Surface-active adjuvants such as salts of bile acids or animal or vegetable phospholipids, but also their mixtures as well as liposomes or their components can be used as vehicle systems.

Especially suitable for oral use are tablets, coated tablets or capsules with talc and/or hydrocarbon vehicles or binders, such as, for example, lactose, corn or potato starch. The use can even take place in liquid form, such as, for example, as juice, to which a sweetener is optionally added.

The dosage of the active ingredients can vary depending on method of administration, age and weight of the patient, type and severity of the disease to be treated and similar factors. The daily dose is 0.5–1000 mg, preferably 50–200 mg, and the dose can be administered as a single dose to be administered once or subdivided into 2 or more daily doses.

The production of the compounds according to the invention takes place according to methods known in the art. For example, compounds of formula I are achieved in that a) a compound of formula II or III

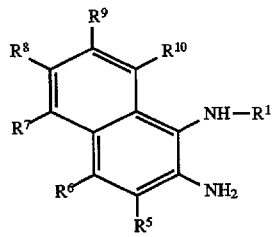

(II)

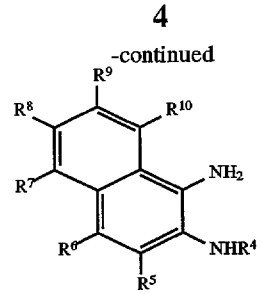

(III)

in which $R^1$ to $R^{10}$ have the above-mentioned meaning, is cyclized with oxalic acid or reactive oxalic acid derivatives or b) a compound of formula IV or V

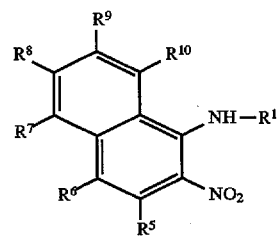

(IV)

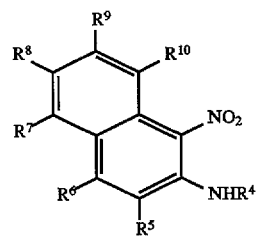

(V)

in which $R^1$ to $R^{10}$ have the above-mentioned meaning, is reacted with oxalic acid or reactive oxalic acid derivatives and after reduction of the nitro group is cyclized or c) a compound of formula VI

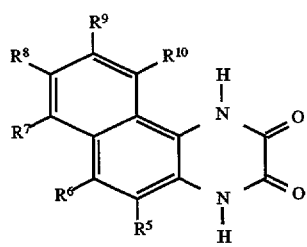

(VI)

in which $R^5$ to $R^{10}$ have the above-mentioned meaning is reacted in the presence of a base with $R^1 Z$ or $R^4 Z$, in which Z represents a leaving group, and then optionally the ester group is saponified or the acid group is esterified or amidated or the nitro group is reduced to the amino group or the amino group is alkylated or acylated or the amino group is exchanged for halogen or cyano or a nitro group or halogen is introduced or a nitrile is converted into the tetrazole or amidoxime or nucleophilically substituted or the isomers are separated or the salts are formed.

The cyclization of the compounds of formulas II and III takes place in one stage or else in two stages with oxalic acid or a reactive oxalic acid derivative. Regarded as preferable is the two-stage process, in which the diamine is reacted with an oxalic acid derivative such as oxalic ester semichloride or reactive oxalic acid imidazolide derivatives in polar solvents such as cyclic or acyclic ethers or halogenated hydrocarbons, for example, tetrahydrofuran, diethyl ether or methylene chloride in the presence of a base such as organic amines, for example, triethylamine, pyridine, Hünig base or diethylaminopyridine. The subsequent cyclization can be performed in a basic or else acidic manner, but preferably in an acid environment, and alcohol can be added to the solvent.

Alkali hydrides, such as NaH, that are used in inert solvents, for example, hydrocarbons and ethers such as dimethoxyethane, THF, i.a., also represent suitable bases for the two-stage process.

In process variant b), after the acylation with oxalic acid or the reactive oxalic acid derivative, in the usual way, the nitro group is reduced catalytically or by reduction with iron powder in acetic acid at higher temperatures or else with sodium sulfide and ammonium hydroxide in alcohol and is cyclized as described above.

The introduction of substituents $R^1$ and $R^4$ takes place according to process c) according to usual alkylation methods by reacting the quinoxalinedione with $R^1$- or $R^4$-Z, in which Z, for example, means tosylate, mesylate, triflate, nonaflate or halogen, in the presence of bases at room temperature or higher temperature in aprotic solvents. The anion can also be produced before $R^1$- or $R^4$-Z is added. As bases, for example, alkali compounds such as potassium carbonate, sodium hydroxide, alkali alcoholates and especially metal hydrides such as sodium hydride are suitable. Optionally, the alkali compounds can also be reacted under phase transfer conditions. If mixtures of compounds with substituent $R^1$ or $R^4$ are obtained, they are separated in the usual way. Aprotic polar solvents, such as dimethylformamide, N-methylpyrrolidone, but also cyclic ethers, such as dioxane or tetrahydrofuran, are suitable solvents for the reaction.

If the reaction takes place in process variant c) with 2 mol of $R^1$-Z under otherwise analogous reaction conditions, then substituents $R^1$ and $R^4$ are introduced at the same time.

The optionally subsequent saponification of an ester group can take place in a basic or preferably acidic manner, by hydrolyzing the reaction mixture at a higher temperature up to the boiling temperature in the presence of acids such as highly concentrated aqueous hydrochloric acid in solvents, such as, for example, trifluoroacetic acid or alcohols. Phosphonic acid esters are preferably hydrolyzed by heating in highly concentrated aqueous acids, such as, for example, concentrated hydrochloric acid or by treatment with a trimethylsilyl halide and subsequent treatment with water.

The esterification of the carboxylic acid or phosphonic acid takes place in a way known in the art with the corresponding alcohol in acid or in the presence of an activated acid derivative. As activated acid derivatives, for example, acid chloride, acid imidazolide or acid anhydride are suitable. In the case of the phosphonic acids, the esterification can be achieved by reaction with orthoesters, optionally with addition of catalysts such as p-toluenesulfonic acid.

The amidation takes place on the free acids or on their reactive derivatives, such as, for example, acid chlorides, mixed anhydrides, imidazolides or azides by reaction with the corresponding amines at room temperature.

The reduction of the nitro group to the amino group takes place catalytically in polar solvents at room temperature or a higher temperature under hydrogen pressure. Metals such as Raney nickel or noble metal catalysts such as palladium or platinum, optionally in the presence of barium sulfate or on vehicles, are suitable as catalysts. Instead of hydrogen, ammonium formate can also be used in a known way. Reducing agents such as tin(II)chloride or titanium(III) chloride can be used just as complex metal hydrides possibly in the presence of heavy metal salts. It can be advantageous to introduce the ester group before the reduction. Nitro groups can also be selectively reduced with $Na_2S$ or sodium dithionite in the usual way.

If an alkylation of an amino group is desired, alkylation can be performed according to usual methods, for example, with alkyl halides or according to the Mitsonubo variant by reaction with an alcohol in the presence of triphenylphosphine and azodicarboxylic acid ester or the amine can be subjected to a reductive amination with aldehydes or ketones optionally in succession with two different carbonyl compounds, and mixed derivatives are obtained (literature, e.g., Verardo et al., Synthesis 1993, 121; Synthesis 1991, 447; Kawaguchi, Synthesis 1985, 701; Micovic et al. Synthesis 1991, 1043).

The acylation of an amino group takes place in the usual way, for example, with an acid halide or acid anhydride optionally in the presence of a base such as dimethylaminopyridine in solvents such as methylene chloride, tetrahydrofuran or pyridine or according to the Scotten Baumann reaction.

The introduction of the cyano group can take place with the help of the Sandmeyer reaction; for example, the diazonium salts, intermediately formed from the amino compounds with nitrites, can be reacted with alkali cyanides in the presence of Cu—I-cyanide.

The introduction of the halogens chlorine, bromine or iodine by the amino group can take place, for example, also according to Sandmeyer, by the diazonium salts formed intermediately with nitrites being reacted with Cu(I)chloride or Cu(I)bromide in the presence of the corresponding acid such as hydrochloric acid or hydrobromic acid or with potassium iodide.

If an organic nitrous acid ester is used, the halogens can be introduced, e.g., with addition of methylene iodide or tetrabromomethane in a solvent such as, for example, dimethylformamide.

The introduction of fluorine is possible, for example, by Balz Schiemann reaction of the diazonium tetrafluoroborate.

The introduction of an $NO_2$ group is possible by a series of known nitration methods. For example, nitration can be performed with nitronium tetrafluoroborate in inert solvents, such as halogenated hydrocarbons or in sulfolane, glacial acetic acid or acetonitrile. The introduction is also possible, e.g., by nitrating acid in water or concentrated sulfuric acid as solvent at temperatures between 0° C. and 30° C.

The introduction of halogen is possible by known halogenation methods, such as, e.g., by electrophilic aromatic substitution.

For example, iodization can be performed according to a process with iodine and iodic acid of Wirth et al. [Liebigs Ann. Chem. 634, 84 (1960)] or with N-iodosuccinimide in solvents such as tetrahydrofuran, dimethylformamide or trifluoromethane sulfonic acid.

The introduction of the tetrazole is made possible by reaction of the corresponding nitrile with an azide such as, e.g., trimethylsilyl azide, hydrazoic acid or sodium azide, optionally with addition of a proton source, such as, e.g., ammonium chloride or triethylammonium chloride in polar solvents such as dimethylformamide, dimethylacetamide or N-methylpyrrolidone at temperatures up to boiling point of the solvent.

Amidoximes are produced from the corresponding nitrile with hydroxylamine hydrochloride, for example, in alcohol-water mixtures, as solvent.

The nucleophilic substitution is performed according to methods known in the literature in the presence of a base and is fostered by an activating electron-attracting group such as, e.g., nitro, cyano, trifluoromethyl, preferably in o-position. As nucleophiles, for example, primary and secondary amines, N-containing unsaturated and saturated heterocycles, cyanide, alcoholates, thiolates, i.a., are suitable. The reaction can be performed in polar solvents such as alcohols, halogenated hydrocarbons, dimethylacetamide, acetonitrile or water or without solvents. As bases, inorganic bases such as alkali or alkaline-earth hydroxides or carbonates or organic bases such as cyclic, acyclic and aromatic amines, such as DBU, Hünig base, pyridine or dimethylaminopyridine are suitable. In the case of amines, the nucleophile itself can be used in excess as base and optionally it is possible to work without any further solvent. For example, the activated sulfonic acid derivative, such as sulfonic acid chloride, can be reacted in the usual way with nucleophilic N derivatives (such as $H_2N(C_{1-4}$ alkyl) or $H_2N-CH_2CONH_2$ or $H_2N-CH_2-R^2$) or with nucleophlic C derivatives (such as $CF_3$ anion or $CH_2-CONH_2$ anion).

The mixtures of isomers can be separated according to usual methods such as, for example, crystallization, chromatography or salt formation in the enantiomers and E/Z isomers.

The production of the salts takes place in the usual way, by mixing a solution of the compound of formula I with the equivalent amount or an excess of an alkali or alkaline-earth compound, which optionally is in solution, and the precipitate being separated or the solution being worked up in the usual way.

If the production of the starting compounds is not described, the latter are known or can be produced analogously to known compounds, such as, for example, according to WO 93/08171 or according to processes described here.

The following processes are to explain the production of the compounds according to the invention:

EXAMPLE 1

(6-Nitro-2,3-dioxo-1,2,3,4-tetrahydrobenzo[f] quinoxalin-1-yl)-methanephosphonic acid The synthesis of 2,4-dinitro-1-fluorophthaline takes place as described in the literature: J. Chem. Soc. 1962, 2616

The synthesis of 2,4-dinitro-1-chloronaphthalene takes place as described in the literature: Reports 1908, 41, 3932

The synthesis of toluenesulfonic acid-(2,4-dinitronaphth-1-ol)-ester takes place as described in the literature: Reports 1908, 41, 3932 a) Trifluoromethanesulfonic acid-(2,4-dinitronaphth-1-ol)-ester 2 g of 2,4-dinitronaphth-1-ol (Martius yellow) is mixed in 30 ml of dichloromethane with 1.72 ml=1.2 equivalents of trifluoromethanesulfonic anhydride and 1.43 ml of triethylamine and stirred at room temperature until the feedstock disappears. It is diluted with dichloromethane, neutralized, washed with brine and the solvent is removed. The crude product is recrystallized from hot ethanol. 89% of product is obtained.

Analogously, there is produced from nonafluorobutanesulfonyl fluoride in toluene:

Nonafluorobutanesulfonic acid-(2,4-dinitronaphth-1-ol)-ester b) (2,4 Dinitro-1-naphthylamino)-methanephosphonic acid diethyl ester 4 g of 2,4 dinitro-1-chloronaphthalene (15.84 mmol) is dissolved in 6.5 g of aminomethanephosphonic acid diethyl ester and 4 g of diphenylmethane and stirred for 72 hours at room temperature. The batch is diluted with methylene chloride, washed with 1N NaOH and washed twice with brine, dried and spun in. The crude product is chromatographed on silica gel with 3.5 liters of cyclohexane and ethyl acetate 1:1 as mobile solvent. 68% of product is obtained in several fractions as viscous oil. NMR (DMSO, delta in ppm): 1.15(6H,tr), 4(4H dq)4.25 (2H m), 7.8, 7.98, 8.9, 9.05 each 1H, 8.6 (2H,d)

Produced in the same way are:

1-Phenyl-1-(2,4 dinitro-1-naphthylamino)-methanephosphonic acid diethyl ester 1-(2,4 dinitro-1-naphthylamino)-ethane-1-phosphonic acid diethyl ester 1-(2,4 dinitro-1-naphthylamino)-propane-1-phosphonic acid diethyl ester 1-(2,4 dinitro-1-naphthylamino)-butane-1-phosphonic acid diethyl ester 1-(2,4 dinitro-1-naphthylamino)-hexane-1-phosphonic acid diethyl ester c) (2-Amino-4-nitro-1-naphthylamino)-methanephosphonic acid diethyl ester 1.352 g of (2,4 dinitro-1-naphthylamino)-methanephosphonic acid diethyl ester is dissolved in 32 ml of ethanol and 23 ml of water, to it is added 4.4 ml of 25% ammonium hydroxide solution, 1.61 g of ammonium chloride and 2.81 g of 35% sodium sulfide and the solution is heated for a few hours to 90° C. The ethanol-water mixture is concentrated by evaporation on a rotary evaporator, taken up in water, extracted with ethyl acetate, washed with brine, dried and spun in. The crude product is chromatographed on silica gel with 2 liters of cyclohexane and ethyl acetate 1:1 and 1 liter of pure ethyl acetate as mobile solvent. 262 mg of product is obtained in several fractions as brown solid.

Produced in the same way are:

1-(2-Amino-4-nitro-1-naphthylamino)-ethane-1-phosphonic acid diethyl ester 1-(2-amino-4-nitro-1-naphthylamino)-butane-1-phosphonic acid diethyl ester 1-(2-amino-4-nitro-1-naphthylamino)-hexane-1-phosphonic acid diethyl ester 1-phenyl-1-(2-amino-4-nitro-1-naphthylamino)-methanephosphonic acid diethyl ester 1-(2-amino-4-nitro-1-naphthylamino)-propane-1-phosphonic acid diethyl ester (79% yield)

d) (6-Nitro-2,3-dioxo-1,2,3,4-tetrahydrobenzo[f] quinoxalin-1-yl)-methanephosphonic acid diethyl ester 100 mg of (2-amino-4-nitro-1-naphthylamino)-methanephosphonic acid diethyl ester is dissolved in a few ml of tetrahydrofuran and treated with 95 microliters of distilled ethyloxalyl chloride and 118 microliters of triethylamine at ice-bath temperature. The solution is stirred first to room temperature and then the reaction is allowed to be completed at 55° oil bath temperature. The batch is concentrated by evaporation, taken up in ethyl acetate and washed with brine, dried and spun in. The crude product is chromatographed on silica gel with ethanol as mobile solvent. 76 mg or 67% of theory of product is obtained as polar fraction. NMR (DMSO,Delta in ppm): 1.03 (6H tr), 3.8 (4H dq), 4.93 (2H d), 7.73 (2H dd), 8.2, 8.35, 8.47 each 1H.

Produced in the same way are:

1-(6-Nitro-2,3-dioxo-1,2,3,4-tetrahydrobenzo[f] quinoxalin-1-yl)-ethane-1-phosphonic acid diethyl ester of melting point >300° (decomposition)

1-(6-nitro-2,3-dioxo-1,2,3,4-tetrahydrobenzo[f] quinoxalin-1-yl)-propane-1-phosphonic acid diethyl ester of melting point >300° (decomposition)

1-(6-nitro-2,3-dioxo-1,2,3,4-tetrahydrobenzo[f]
quinoxalin-1-yl)-butane-1-phosphonic acid diethyl
ester 1-(6-nitro-2,3-dioxo-1,2,3,4-tetrahydrobenzo[f]
quinoxalin-1-yl)-hexane-1-phosphonic acid diethyl
ester 1-phenyl-1-(6-nitro-2,3-dioxo-1,2,3,4-tetrahydrobenzo[f]
quinoxalin-1-yl)-methanephosphonic acid diethyl ester e) (6-Nitro-2,3-dioxo-1,2,3,4-tetrahydrobenzo[f]quinoxalin-1-yl)-methanephosphonic acid 32 mg of (6-nitro-2,3-dioxo-1,2,3,4-tetrahydrobenzo[f] quinoxalin-1-yl)-methanephosphonic acid diethyl ester is introduced in 2 ml of acetonitrile under nitrogen at room temperature. 80 microliters of trimethylsilylbromide is instilled with a syringe. The solution is stirred for 20 hours at room temperature and concentrated by evaporation. The residue is suspended in a little water, suctioned off and washed with water. After drying of the crude product, 21 mg of phosphonic acid is obtained. NMR (DMSO,Delta in ppm): 4.7 (2H d), 7.65 (2H m), 8.2 (1H, m) 8.44 (2H). Melting point >340°

In a corresponding way, there are produced:

1-(6-Nitro-2,3-dioxo-1,2,3,4-tetrahydrobenzo[f]
quinoxalin-1-yl)-ethane-1-phosphonic acid with melting point >300° C.

1-(6-nitro-2,3-dioxo-1,2,3,4-tetrahydrobenzo[f]
quinoxalin-1-yl)-propane-1-phosphonic acid with melting point >300° C.

1-(6-nitro-2,3-dioxo-1,2,3,4-tetrahydrobenzo[f]
quinoxalin-1-yl)-butane-1-phosphonic acid 1-(6-nitro-2,3-dioxo-1,2,3,4-tetrahydrobenzo[f]
quinoxalin-1-yl)-hexane-1-phosphonic acid 1-phenyl-1-(6-nitro-2,3-dioxo-1,2,3,4-tetrahydrobenzo[f]
quinoxalin-1-yl)-methanephosphonic acid

EXAMPLE 2

1-(2,4 Dinitro-1-naphth-yl-[N-ethoxyoxalyl]amino)-propane-1-phosphonic acid diethyl ester A total of 1.2 mmol of triethylamine as well as 1.2 mmol of ethyl oxalyl chloride are added little by little to 100 mg (0.24 mmol) of 1-(2,4 dinitro-1-naphthylamino)-propane-1-phosphonic acid diethyl ester in 1.5 ml of tetrahydrofuran and stirred for a total of 20 hours at 80° oil bath temperature. The solvent is concentrated by evaporation, the crude product is divided between water and a lot of ethyl acetate, the organic phase is washed with brine, dried and spun in. The mixture that is produced is chromatographed on silica gel with ethyl acetate as mobile solvent. 24 mg of product as well as some feedstock is obtained as polar fraction.

Analogously, 2,4 dinitro-1-naphth-yl-[N-ethoxyoxalyl] aminomethanephosphonic acid diethyl ester is produced.

EXAMPLE 3

(6,10-Dinitro-2,3-dioxo-1,2,3,4-tetrahydrobenzo[f]
quinoxalin-1-yl)-methanephosphonic acid a) (6,10-Dinitro-2,3-dioxo-1,2,3,4-tetrahydrobenzo[f]
quinoxalin-1-yl)-methanephosphonic acid diethyl ester 90 mg of (6-nitro-2,3-dioxo-1,2,3,4-tetrahydrobenzo[f]
quinoxalin-1-yl)-methanephosphonic acid diethyl ester is dissolved in 1 ml of methylene chloride and stirred with 30 mg of nitronium tetrafluoroborate at ice bath temperature and later at room temperature.

It is adjusted to pH 8 with sodium bicarbonate solution, the organic phase is washed with brine, dried and spun in. The mixture that is produced is chromatographed on silica gel. 24 mg of product is obtained.

Analogously, 1-(6,10-Dinitro-2,3-dioxo-1,2,3,4-tetrahydrobenzo[f]quinoxalin-1-yl)-ethane-1-phosphonic acid diethyl ester is produced.

b) In an analogous performance, the ester is saponified as described in Example 1e).

(6,10-Dinitro-2,3-dioxo-1,2,3,4-tetrahydrobenzo[f]
quinoxalin-1-yl)-methanephosphonic acid and analogously 1-(6,10-dinitro-2,3-dioxo-1,2,3,4-tetrahydrobenzo[f]
quinoxalin-1-yl)-ethane-1-phosphonic acid are obtained.

EXAMPLE 4

(6-Nitro-7-sulfamoyl-2,3-dioxo-1,2,3,4-
tetrahydrobenzo[f]quinoxalin-1-yl)-
methanephosphonic acid and (7-sulfamoyl-2,3-
dioxo-1,2,3,4-tetrahydrobenzo[f]quinoxalin-1-yl)-
methanephosphonic acid a) 2-Nitro-5-sulfonamido-naphth-1-ol and 2,4 dinitro-5-sulfonamido-naphth-1-ol 1 g of 5-sulfonamidonaphth-1-ol is nitrated with a mixture of nitric acid and water with ice bath cooling. The mixture is neutralized with solid sodium bicarbonate, extracted with a lot of methylene chloride, washed with brine, dried and spun in. The mixture that is produced is chromatographed on silica gel. A mixture of 2-nitro-5-sulfonamido-naphth-1-ol and 2,4 dinitro-5-sulfonamido-naphth-1-ol results. NMR (DMSO,Delta in ppm): 7.8 (4H m), 8.2 (2H m), 8.4 (1H, d), 8.7 (1H d) and 7.05 (2H s), 7.6 (1H dd), 8.3 (1H d), 8.5 (1H, d) 8.8 (1H s) for the dinitronaphthol.

b) The toluenesulfonic acid esters are produced in an analogous performance as described in the literature.

There are obtained

Toluenesulfonic acid-(2,4 dinitro-5-sulfonamido-naphth-1-ol)-ester as well as toluenesulfonic acid-(2-nitro-5-sulfonamido-naphth-1-ol)-ester.

c) The esters are reacted with aminoalkanephosphonic acid diethyl esters in an analogous performance as described in Example 1b). Thus produced are 1-Phenyl-1-(2,4 dinitro-5-sulfamoyl-1-naphthylamino)-methanephosphonic acid diethyl ester 1-methyl-1-(2,4 dinitro-5-sulfamoyl-1-naphthylamino)-ethane-1-phosphonic acid diethyl ester (2,4 dinitro-5-sulfamoyl-1-naphthylamino)-methanephosphonic acid diethyl ester 1-(2,4 dinitro-5-sulfamoyl-1-naphthylamino)-propane-1-phosphonic acid diethyl ester or 1-phenyl-1-(2-nitro-5-sulfamoyl-1-naphthylamino)-methanephosphonic acid diethyl ester 1-methyl-1-(2-nitro-5-sulfamoyl-1-naphthylamino)-ethane-1-phosphonic acid diethyl ester (2-nitro-5-sulfamoyl-1-naphthylamino)-methanephosphonic acid diethyl ester 1-(2-nitro-5-sulfamoyl-1-naphthylamino)-propane-1-phosphonic acid diethyl ester d) With the same methods as described in Example 1c), there are obtained 1-Phenyl-1-(2-amino-4-nitro-5-sulfamoyl-1-naphthylamino)-methanephosphonic acid diethyl ester 1-methyl-1-(2-amino-4-nitro-5-sulfamoyl-1-naphthylamino)-ethane-1-phosphonic acid diethyl ester (2-amino-4-nitro-5-sulfamoyl-1-naphthylamino)-methanephosphonic acid diethyl ester 1-(2-amino-4-nitro-5-sulfamoyl-1-naphthylamino)-
propane-1-phosphonic acid diethyl ester or 1-phenyl-1-(2-amino-5-sulfamoyl-1-naphthylamino)-
methanephosphonic acid diethyl ester 1-methyl-1-(2-amino-5-sulfamoyl-1-naphthylamino)-
ethane-1-phosphonic acid diethyl ester (2-amino-5-sulfamoyl-1-naphthylamino)-
methanephosphonic acid diethyl ester 1-(2-amino-5-sulfamoyl-1-naphthylamino)-propane-1-
phosphonic acid diethyl ester e) By reaction with reactive oxalic acid derivatives as described, e.g., in Example 1d) or according to known processes, there are produced 1-(6-Nitro-7-sulfamoyl-2,3-dioxo-1,2,3,4-
tetrahydrobenzo[f]quinoxalin-1-yl)-ethane-1-
phosphonic acid diethyl ester 1-(6-nitro-7-sulfamoyl-2,3-dioxo-1,2,3,4-
tetrahydrobenzo[f]quinoxalin-1-yl)-propane-1-
phosphonic acid diethyl ester 1-phenyl-1-(6-nitro-7-sulfamoyl-2,3-dioxo-1,2,3,4-
tetrahydrobenzo[f]quinoxalin-1-yl)-
methanephosphonic acid diethyl ester (6-nitro-7-sulfamoyl-2,3-dioxo-1,2,3,4-tetrahydrobenzo
[f]quinoxalin-1-yl)-methanephosphonic acid diethyl
ester as well as 1-(7-sulfamoyl-2,3-dioxo-1,2,3,4-tetrahydrobenzo[f]
quinoxalin-1-yl)-ethane-1-phosphonic acid diethyl
ester 1-(7-sulfamoyl-2,3-dioxo-1,2,3,4-tetrahydrobenzo[f]
quinoxalin-1-yl)-propane-1-phosphonic acid diethyl
ester 1-phenyl-1-(7-sulfamoyl-2,3-dioxo-1,2,3,4-
tetrahydrobenzo[f]quinoxalin-1-yl)-
methanephosphonic acid diethyl ester (7-sulfamoyl-2,3-dioxo-1,2,3,4-tetrahydrobenzo[f]
quinoxalin-1-yl)-methanephosphonic acid diethyl ester f) The ester is saponified in an analogous performance as described in Example 1e). There are obtained 1-(6-Nitro-7-sulfamoyl-2,3-dioxo-1,2,3,4-
tetrahydrobenzo[f]quinoxalin-1-yl)-ethane-1-
phosphonic acid 1-(6-nitro-7-sulfamoyl-2,3-dioxo-1,2,3,4
-tetrahydrobenzo[f]quinoxalin-1-yl)-propane-1-
phosphonic acid 1-phenyl-1-(6-nitro-7-sulfamoyl-2,3-dioxo-1,2,3,4-
tetrahydrobenzo[f]quinoxalin-1-yl)-
methanephosphonic acid (6-nitro-7-sulfamoyl-2,3-dioxo-1,2,3,4-tetrahydrobenzo
[f]quinoxalin-1-yl)-methanephosphonic acid as well as 1-(7-sulfamoyl-2,3-dioxo-1,2,3,4-tetrahydrobenzo[f]
quinoxalin-1-yl)-ethane-1-phosphonic acid 1-(7-sulfamoyl-2,3-dioxo-1,2,3,4-tetrahydrobenzo[f]
quinoxalin-1-yl)-propane-1-phosphonic acid 1-phenyl-1-(7-sulfamoyl-2,3-dioxo-1,2,3,4-
tetrahydrobenzo[f]quinoxalin-1-yl)-
methanephosphonic acid (7-sulfamoyl-2,3-dioxo-1,2,3,4-tetrahydrobenzo[f]
quinoxalin-1-yl)-methanephosphonic acid

EXAMPLE 5

(6-Nitro-9-sulfamoyl-2,3-dioxo-1,2,3,4-tetrahydrobenzo
[f]quinoxalin-1-yl)-methanephosphonic acid from purchased flavianic acid (5,7-dinitro-8-hydroxy-naphthalene-2-sulfonic acid) is produced analogously after protection of the sulfonic acid.

EXAMPLE 6

1-(6-Nitro-9-sulfamoyl-2,3-dioxo-1,2,3,4-
tetrahydrobenzo[f]quinoxalin-1-yl)-ethane-1-phosphonic acid from purchased flavianic acid (5,7-dinitro-8-hydroxy-naphthalene-2-sulfonic acid) is produced analogously to Example 5.

EXAMPLE 7

(6-Amino-2,3-dioxo-1,2,3,4-tetrahydrobenzo[f]
quinoxalin-1-yl)-methanephosphonic acid from (6-
nitro-2,3-dioxo-1,2,3,4-tetrahydrobenzo[f]
quinoxalin-1-yl)-methanephosphonic acid a) 0.3 mmol of (6-nitro-2,3-dioxo-1,2,3,4-tetrahydrobenzo[f]quinoxalin-1-yl)-methanephosphonic acid diethyl ester in 10 ml of DMF z.A. is dissolved, and 10 mg of platinum oxide catalyst, which was previously saturated with hydrogen, is added. It is hydrogenated with hydrogen for three hours at normal pressure and room temperature. The catalyst is suctioned off on Celite, the mother liquor is diluted with water and the precipitate that is produced is suctioned off. 44% of theory of (6-amino-2,3-dioxo-1,2,3,4-tetrahydro-benzo[f]quinoxalin-1-yl)-methanephosphonic acid diethyl ester is obtained. The latter is described as in Example 1e) or saponified according to standard conditions with HCl to (6-amino-2,3-dioxo-1,2,3,4-tetrahydrobenzo[f]quinoxalin-1-yl)-methanephosphonic acid (or to its hydrochloride, respectively).

Analogously, there is produced (6-amino-2,3-dioxo-1,2,3,4-tetrahydrobenzo[f]quinoxalin-4-yl)-methanephosphonic acid.

b) With use of palladium/barium sulfate catalyst, there are produced analogously:

1-(6-amino-2,3-dioxo-1,2,3,4-tetrahydrobenzo[f]
quinoxalin-1-yl)-acetonitrile from 1-(6-nitro-2,3-
dioxo-1,2,3,4-tetrahydrobenzo[f]quinoxalin-1-yl)-
acetonitrile and 1-(6-amino-2,3-dioxo-1,2,3,4-tetrahydrobenzo[f]
quinoxalin--yl)-acetonitrile from 1-(6-nitro-2,3-dioxo-
1,2,3,4-tetrahydrobenzo[f]quinoxalin-4-yl)-acetonitrile

EXAMPLE 8

(6-Cyano-2,3-dioxo-1,2,3,4-tetrahydrobenzo[f]
quinoxalin-1-yl)-methanephosphonic acid diethyl ester is obtained from (6-amino-2,3-dioxo-1,2,3,4-tetrahydrobenzo[f]quinoxalin-1-yl)-methanephosphonic acid ester by diazotization and Sandmeyer reaction with copper(I)cyanide. After saponification of the ester with known methods, (6-cyano-2,3-dioxo-1,2,3,4-tetrahydrobenzo-[f]quinoxalin-1-yl)-methanephosphonic acid is obtained.

Analogously, (6-cyano-2,3-dioxo-1,2,3,4-
tetrahydrobenzo[f]quinoxalin-4-yl)-methanephosphonic
acid is obtained from (6-cyano-2,3-dioxo-1,2,3,4-
tetrahydrobenzo[f]quinoxalin-4-yl)-methanephosphonic
acid diethyl ester.

EXAMPLE 9

(6-Nitro-7-sulfonamido-2,3-dioxo-1,2,3,4-
tetrahydrobenzo[f]quinoxalin-1-yl)-
methanephosphonic acid diethyl ester and (6-nitro-
7-sulfonamido-2,3-dioxo-1,2,3,4-tetrahydrobenzo[f]
quinoxalin-4-yl)-methanephosphonic acid diethyl
ester 150 mg of 6-nitro-7-sulfonamido-2,3-dioxo-1,2,3,4-tetrahydrobenzo[f]quinoxaline, which can be synthesized according to known methods, is dissolved in 1 ml of dimethylsulfoxide z.A. and 10 equivalents of trifluoromethanesulfonylmethanephosphonic acid diethyl ester, which is produced from the available alcohol 1-hydroxymethanephosphonic acid diethyl ester according to standard methods, is added. After heating the mixture to 160°, it is worked up for several hours. It is diluted with sodium bicarbonate solution, extracted with methylene chloride, dried and concentrated by evaporation. The crude product is chromatographed on silica gel with ethyl acetate and then ethanol.

A base for bonding the trifluoromethanesulfonic acid is optionally added in performing the process.

The new compounds obtained are (6-Nitro-7-sulfonamido-2,3-dioxo-1,2,3,4-tetrahydrobenzo[f]quinoxalin-1-yl)-methanephosphonic acid diethyl ester as well as (6-nitro-7-sulfonamido-2,3-dioxo-1,2,3,4-tetrahydrobenzo[f]quinoxalin-4-yl)-methanephosphonic acid diethyl ester.

Produced in the same way are:

(6-Nitro-8-sulfonamido-2,3-dioxo-1,2,3,4-tetrahydrobenzo[f]quinoxalin-1-yl)-methanephosphonic acid diethyl ester and (6-nitro-8-sulfonamido-2,3-dioxo-1,2,3,4-tetrahydrobenzo[f]quinoxalin-4-yl)-methanephosphonic acid diethyl ester (6-nitro-8,10-disulfonamido-2,3-dioxo-1,2,3,4-tetrahydrobenzo[f]quinoxalin-1-yl)-methanephosphonic acid diethyl ester and (6-nitro-8,10-disulfonamido-2,3-dioxo-1,2,3,4-tetrahydrobenzo[f]quinoxalin-4-yl)-methanephosphonic acid diethyl ester (6-nitro-7-sulfonylmethano-2,3-dioxo-1,2,3,4-tetrahydrobenzo[f]quinoxalin-1-yl)-methanephosphonic acid diethyl ester and (6-nitro-7-sulfonylmethano-2,3-dioxo-1,2,3,4-tetrahydrobenzo[f]quinoxalin-4-yl)-methanephosphonic acid diethyl ester (6-nitro-7-cyano-2,3-dioxo-1,2,3,4-tetrahydrobenzo[f]quinoxalin-1-yl)-methanephosphonic acid diethyl ester and (6-nitro-7-cyano-2,3-dioxo-1,2,3,4-tetrahydrobenzo[f]quinoxalin-4-yl)-methanephosphonic acid diethyl ester (6-nitro-8-cyano-2,3-dioxo-1,2,3,4-tetrahydrobenzo[f]quinoxalin-1-yl)-methanephosphonic acid diethyl ester and (6-nitro-8-cyano-2,3-dioxo-1,2,3,4-tetrahydrobenzo[f]quinoxalin-4-yl)-methanephosphonic acid diethyl ester (6-nitro-7-bromo-2,3-dioxo-1,2,3,4-tetrahydrobenzo[f]quinoxalin-1-yl)-methanephosphonic acid diethyl ester and (6-nitro-7-bromo-2,3-dioxo-1,2,3,4-tetrahydrobenzo[f]quinoxalin-4-yl)-methanephosphonic acid diethyl ester (6-nitro-7-trifluoromethyl-2,3-dioxo-1,2,3,4-tetrahydrobenzo[f]quinoxalin-1-yl)-methanephosphonic acid diethyl ester and (6-nitro-7-trifluoromethyl-2,3-dioxo-1,2,3,4-tetrahydrobenzo[f]quinoxalin-4-yl)-methanephosphonic acid diethyl ester

EXAMPLE 10

(6-Nitro-2,3-dioxo-1,2,3,4-tetrahydrobenzo[f]quinoxalin-4-yl)-methanephosphonic acid The synthesis of 1-nitro-2-fluoronaphthalene takes place as described in the literature.

The synthesis of 1-nitro-2-chloronaphthalene takes place as described in the literature.

1-Nitro-2-hydroxynaphthalene can be purchased or produced by oxidation of nitroso-2-hydroxynaphthalene.

a) Toluenesulfonic acid-(1-nitronaphth-2-ol)-ester 5 g of 1-nitronaphth-1-ol is dissolved in 30 ml of triethylamine with 5.54 g=1.1 equivalents of toluenesulfonic acid chloride at 60° and stirred at this temperature until the feedstock disappears. The mixture is allowed to cool, is suctioned off and the precipitate is washed with cold ethanol. The crude product is recrystallized from hot ethyl acetate. 9.1 g of product is obtained. NMR(DMSO): 2.44 (3H s), 7.5 (3H d), 7.8 (5H,m) 8.17 (1H m), 8.34 (1H d).

Produced in a known way:

Nonafluorobutanesulfonic acid-(1-nitronaphth-2-ol)-ester trifluoromethanesulfonic acid-(1-nitronaphth-2-ol)-ester methanesulfonic acid-(1-nitronaphth-2-ol)-ester b) (1-Nitro-2-naphthylamino)-methanephosphonic acid diethyl ester 450 mg of toluenesulfonic acid-(1-nitronaphth-2-ol)-ester is dissolved in 436 mg of aminomethanephosphonic acid diethyl ester and 0.6 g of diphenylmethane and stirred for 72 hours at 40°–60°. The batch is diluted with methylene chloride, washed with 1N NaOH and twice with brine, dried and spun in. The crude product is chromatographed on silica gel with hexane and ethyl acetate 1:1 as mobile solvent. In addition to 60% feedstock, 31% of product is obtained as viscous, dark oil.

Produced in the same way are:

1-Phenyl-1-(1-nitro-2-naphthylamino)-methanephosphonic acid diethyl ester 1-(1-nitro-2-naphthylamino)-ethane-1-phosphonic acid diethyl ester 1-(1-nitro-2-naphthylamino)-propane-1-phosphonic acid diethyl ester 1-(1-nitro-2-naphthylamino)-butane-1-phosphonic acid diethyl ester c) (1-Amino-2-naphthylamino)-methanephosphonic acid diethyl ester 170 mg of (1-nitro-2-naphthylamino)-methanephosphonic acid diethyl ester is reduced in 2 ml of glacial acetic acid with 10 equivalents of iron powder. After two hours, the mixture becomes viscous and then solid. It is diluted with ethyl acetate, the iron is removed, and it is chromatographed with ethyl acetate. The product is obtained in 60% yield.

Produced in the same way are:

1-Phenyl-1-(1-amino-2-naphthylamino)-methanephosphonic acid diethyl ester 1-(1-amino-2-naphthylamino)-ethane-1-phosphonic acid diethyl ester 1-(1-amino-2-naphthylamino)-propane-1-phosphonic acid diethyl ester 1-(1-amino-2-naphthylamino)-butane-1-phosphonic acid diethyl ester d) As described in Example 1, the amines are cyclized with oxalic acid derivatives to 1-Phenyl-1-(2,3-dioxo-1,2,3,4-tetrahydrobenzo[f]quinoxalin-yl)-methanephosphonic acid diethyl ester 1-(2,3-dioxo-1,2,3,4-tetrahydrobenzo[f]quinoxalin-yl)-ethane-1-phosphonic acid diethyl ester 1-(2,3-dioxo-1,2,3,4-tetrahydrobenzo[f]quinoxalin-yl)-methanephosphonic acid diethyl ester 1-(2,3-dioxo-1,2,3,4-tetrahydrobenzo[f]quinoxalin-yl)-propane-1-phosphonic acid diethyl ester 1-(2,3-dioxo-1,2,3,4-tetrahydrobenzo[f]quinoxalin-yl)-
butane-1-phosphonic acid diethyl ester
e) Nitration of the phosphonates leads to
1-(6-Nitro-2,3-dioxo-1,2,3,4-tetrahydrobenzo[f]
quinoxalin-yl)-ethane-1-phosphonic acid diethyl ester
of melting point >300° (decomposition)
1-(6-nitro-2,3-dioxo-1,2,3,4-tetrahydrobenzo[f]
quinoxalin-yl)-methanephosphonic acid diethyl ester
of melting point 243° C.
1-(6-nitro-2,3-dioxo-1,2,3,4-tetrahydrobenzo[f]
quinoxalin-yl)-propane-1-phosphonic acid diethyl ester
1-(6-nitro-2,3-dioxo-1,2,3,4-tetrahydrobenzo[f]
quinoxalin-yl)-butane-1-phosphonic acid diethyl ester
1-phenyl-1-(6-nitro-2,3-dioxo-1,2,3,4-tetrahydrobenzo[f]
quinoxalin-4-yl)-methanephosphonic acid diethyl ester
f) Saponification to phosphonic acids analogously to Example 1e). Obtained are
1-(6-Nitro-2,3-dioxo-1,2,3,4-tetrahydrobenzo[f]
quinoxalin-yl)-ethane-1-phosphonic acid of melting point >300° (decomposition) NMR(DMSO): 1.7 (3H d) 5.85 (1H), 7.8 (2H m), 8.5, 8.8, 9.4 each 1H
1-(6-nitro-2,3-dioxo-1,2,3,4-tetrahydrobenzo[f]
quinoxalin-yl)-methanephosphonic acid. NMR (DMSO): 4.7(2H d), 7.8 (2H m), 8.5, 8.7, 8.8 each 1H
1-(6-nitro-2,3-dioxo-1,2,3,4-tetrahydrobenzo[f]
quinoxalin-yl)-propane-1-phosphonic acid of melting point >300° (decomposition)
1-(6-nitro-2,3-dioxo-1,2,3,4-tetrahydrobenzo[f]
quinoxalin-yl)-butane-1-phosphonic acid
1-phenyl-1-(6-nitro-2,3-dioxo-1,2,3,4-tetrahydrobenzo[f]
quinoxalin-4-yl)-methanephosphonic acid

EXAMPLE 11

1-(6-Sulfonamido-2,3-dioxo-1,2,3,4-tetrahydrobenzo[f]
quinoxalin-4-yl)-methanephosphonic acid is produced according to processes further described above from amino-3-hydroxy-naphthalene-1-sulfonic acid. 1-(6-Sulfonamido-2,3-dioxo-1,2,3,4-tetrahydrobenzo[f]quinoxalin-4-yl)-ethane-1-phosphonic acid is synthesized analogously.

EXAMPLE 12

1-(8-Sulfonamido-2,3-dioxo-1,2,3,4-tetrahydrobenzo[f]
quinoxalin-4-yl)-methanephosphonic acid is produced according to processes further described above from 6-hydroxy-naphthalene-2-sulfonic acid salt. 1-(8-Sulfonamido-2,3-dioxo-1,2,3,4-tetrahydrobenzo[f]
quinoxalin-4-yl)-ethane-1-phosphonic acid is synthesized analogously.

EXAMPLE 13

Analogously and with the methods usual for amino acids, by using commercially available amino acids and their derivatives, for example, tert-butyl esters, the following compounds are produced by way of example:

(6-Nitro-2,3-dioxo-1,2,3,4-tetrahydrobenzo[f]quinoxalin-1-yl)-methanecarboxylic acid
(6-nitro-7-sulfamoyl-2,3-dioxo-1,2,3,4-tetrahydrobenzo[f]quinoxalin-1-yl)-methanecarboxylic acid
(7-sulfamoyl-2,3-dioxo-1,2,3,4-tetrahydrobenzo[f]quinoxalin-1-yl)-methanecarboxylic acid
(6-nitro-2,3-dioxo-1,2,3,4-tetrahydrobenzo[f]quinoxalin-yl)-methanecarboxylic acid
1-(6-nitro-2,3-dioxo-1,2,3,4-tetrahydrobenzo[f]quinoxalin-1-yl)-ethane-1-carboxylic acid
1-(6-nitro-7-sulfamoyl-2,3-dioxo-1,2,3,4-tetrahydrobenzo[f]quinoxalin-1-yl)-ethane-1-carboxylic acid
1-(7-sulfamoyl-2,3-dioxo-1,2,3,4-tetrahydrobenzo[f]quinoxalin-1-yl)-ethane-1-carboxylic acid
1-(6-nitro-2,3-dioxo-1,2,3,4-tetrahydrobenzo[f]quinoxalin-yl)-ethane-1-carboxylic acid

EXAMPLE 14

1-(6-Nitro-2,3-dioxo-1,2,3,4-tetrahydrobenzo[f]
quinoxalin-yl)-acetonitrile a) 1-Nitro-2-naphthylamino-acetonitrile 32.1 g of 1-aminoacetonitrile produced according to known specifications is added to 21.58 g (80.7 mmol) of methanesulfonic acid-(1-nitronaphth-2-ol)-ester. It is stirred for 8 hours at 60°, then diluted with dichloromethane and the mixture is applied to a column filled with silica gel. Chromatography with toluene yields, in addition to 7 g of 1-nitronaphth-2-ol, 13% of theory of (1-nitro-2-naphthylamino)-acetonitrile.

Obtained in the same way are:

(1-Nitro-2-naphthylamino)-methyl-acetonitrile
(1-nitro-2-naphthylamino)-1,1-dimethyl-acetonitrile.

b) (1-Amino-2-naphthyl)aminoacetonitrile 0.45 g of 1-nitro-2-naphthylamino-acetonitrile is hydrogenated at room temperature in 65 ml of dioxane on Pd/barium sulfate as catalyst. After removal of the catalyst, 100% crude product of (1-amino-2-naphthyl) aminoacetonitrile is obtained.

Obtained analogously are:

(1-Amino-2-naphthylamino)-methyl-acetonitrile
(1-amino-2-naphthylamino)-1,1-dimethyl-acetonitrile c) 1-(2,3-Dioxo-1,2,3,4-tetrahydrobenzo[f]quinoxalin-yl)-acetonitrile 0.41 g crude product of (1-amino-2-naphthyl) aminoacetonitrile is reacted analogously to Example 1d) to 0.126 g of 1-(2,3-dioxo-1,2,3,4-tetrahydrobenzo[f]
quinoxalin-yl)-acetonitrile. The melting point is >350°. NMR(DMSO): 5.4 (2H), 7.55(2H), 7.75, 7.89, 8.03, 8.63 each (1H d), 12.24 (1H s).

Obtained analogously are:

1-(2,3-Dioxo-1,2,3,4-tetrahydrobenzo[f]quinoxalin-yl)-methylacetonitrile 1-(2,3-dioxo-1,2,3,4-tetrahydrobenzo[f]quinoxalin-yl)-dimethyl-acetonitrile d) 1-(6-Nitro-2,3-dioxo-1,2,3,4-tetrahydrobenzo[f]
quinoxalin-yl)-acetonitrile 1-(2,3-dioxo-1,2,3,4-tetrahydrobenzo[f]quinoxalin-yl)-acetonitrile is reacted with 65% nitric acid for 3 hours at room temperature. It is precipitated from water, the yellow crystals are washed and 51% of product of melting point >300° is obtained (slow decomposition).
Obtained analogously are:

1-(6-Nitro-2,3-dioxo-1,2,3,4-tetrahydrobenzo[f]
quinoxalin-yl)-methylacetonitrile 1-(6-nitro-2,3-dioxo-1,2,3,4-tetrahydrobenzo[f]
quinoxalin-yl)-dimethyl-acetonitrile

EXAMPLE 15

1-(6-Nitro-2,3-dioxo-1,2,3,4-tetrahydrobenzo[f]
quinoxalin-yl)-methanetetrazole and 1-(2,3-dioxo-1,2,3,4-tetrahydrobenzo[f]quinoxalin-yl)-methanetetrazole 301 mg of 1-(2,3-dioxo-1,2,3,4-tetrahydrobenzo[f] quinoxalin-yl)-acetonitrile is stirred for 2.5 hours at 150° in 12 ml of N-methylpyrrolidone with 3 equivalents of sodium azide as well as 1.5 equivalents of triethylammonium chloride. After dilution and acidification of the cooled mixture, the crystals are suctioned off, washed with water and then acetonitrile and dried. 83% of 1-(2,3-dioxo-1,2,3,4-tetrahydrobenzo[f]quinoxalin-yl)-methanetetrazole of melting point 320° results.

1-(6-Nitro-2,3-dioxo-1,2,3,4-tetrahydrobenzo[f] quinoxalin-yl)-methanetetrazole is produced analogously to Example 14d) from 1-(2,3-dioxo-1,2,3,4-tetrahydrobenzo[f] quinoxalin-yl)-methanetetrazole. Melting point >300°.

EXAMPLE 16

1-(2,3-Dioxo-1,2,3,4-tetrahydrobenzo[f]quinoxalin-yl)-methanecarboxylic acid-amidoxime 100 mg of 1-(2,3-dioxo-1,2,3,4-tetrahydrobenzo[f] quinoxalin-yl)-acetonitrile is refluxed for 4 hours with 2 equivalents of hydroxylamine hydrochloride as well as sodium bicarbonate in 0.2 ml of water as well as a little ethanol. The product is precipitated after dilution with water and suctioned off. Yield 62% NMR(DMSO): 4.9 (2H s), 5.55 (2H s), 7.55 (3H m), 7.75, 7.95, 8.6 each 1H, 9.2OH, 12.2 (1H broad).

EXAMPLE 17

1-(6-Nitro-2,3-dioxo-1,2,3,4-tetrahydrobenzo[f] quinoxalin-1-yl)-acetonitrile and 1-(6-nitro-2,3-dioxo-1,2,3,4-tetrahydrobenzo[f]quinoxalin-1-yl)-acetamide In the same way as in Example 14a), there are obtained from the corresponding methanesulfonic acid ester:
2-Nitro-1-naphthylamino-acetonitrile
(2-nitro-1-naphthylamino)-methyl-acetonitrile
(2-nitro-1-naphthylamino)-1,1-dimethyl-acetonitrile
Obtained analogously are:
(2-Amino-1-naphthylamino)-methyl-acetonitrile
(2-amino-1-naphthyl)aminoacetonitrile
(2-amino-1-naphthylamino)-1,1-dimethyl-acetonitrile
The compounds that are produced from them
1-(2,3-Dioxo-1,2,3,4-tetrahydrobenzo[f]quinoxalin-1-yl)-acetonitrile
NMR(DMSO): 5.2 (2H), 7.45, 7.53, 7.68, 7.83, 8.03, 8.14 each (1H d), 12.2 (1H s).
1-(2,3-dioxo-1,2,3,4-tetrahydrobenzo[f]quinoxalin-1-yl)-methylacetonitrile
1-(2,3-dioxo-1,2,3,4-tetrahydrobenzo[f]quinoxalin-1-yl)-dimethyl-acetonitrile
1-(6-Nitro-2,3-dioxo-1,2,3,4-tetrahydrobenzo[f] quinoxalin-1-yl)-acetamide:
1-(2,3-Dioxo-1,2,3,4-tetrahydrobenzo[f]quinoxalin-1-yl)-acetonitrile is reacted with 65% nitric acid for 3 hours at room temperature. It is precipitated from water, the yellow crystals are washed and approximately 100% crude product is obtained of melting point >300° (slow decomposition). This is 1-(6-Nitro-2,3-dioxo-1,2,3,4-tetrahydrobenzo[f]quinoxalin-1-yl)-acetamide.

1-(6-Nitro-2,3-dioxo-1,2,3,4-tetrahydrobenzo[f] quinoxalin-1-yl)-acetonitrile results with use of nitronium tetrafluoroborate and it melts at >300°.
Obtained analogously are:

1-(6-Nitro-2,3-dioxo-1,2,3,4-tetrahydrobenzo[f] quinoxalin-1-yl)-methylacetonitrile
1-(6-nitro-2,3-dioxo-1,2,3,4-tetrahydrobenzo[f] quinoxalin-1-yl)-dimethyl-acetonitrile

EXAMPLE 18

1-(6-Nitro-2,3-dioxo-1,2,3,4-tetrahydrobenzo[f] quinoxalin-1-yl)-methanetetrazole (melting point 305°–315° decomposition) and 1-(2,3-dioxo-1,2,3,4-tetrahydrobenzo[f]quinoxalin-1-yl)-methanetetrazole (melting point approximately 310° decomposition) are produced as described in Example 15.

EXAMPLE 19

1-(2,3-Dioxo-1,2,3,4-tetrahydrobenzo[f]quinoxalin-1-yl)-methanecarboxylic acid-amidoxime 100 mg of 1-(2,3-dioxo-1,2,3,4-tetrahydrobenzo[f] quinoxalin-1-yl)-acetonitrile is refluxed for 7 hours with 2 equivalents of hydroxylamine hydrochloride as well as sodium bicarbonate in 0.2 ml of water as well as a little ethanol. The product precipitates after dilution with water and is suctioned off. Yield 67%. NMR(DMSO): 4.9 (2H s), 5.7 (2H s), 7.5 (3H m), 7.75, 7.95, 8.4 each 1H, 9.12OH, 12.14 (1H broad).

EXAMPLE 20

[6-(Piperidin-1-yl)-2,3-dioxo-1,2,3,4-tetrahydrobenzo[f]quinoxalin-4-yl]-methanephosphonic acid diethyl ester A mixture of 100 microliters of aqueous glutaric dialdehyde (content about 25%), 300 microliters of diluted sulfuric acid and 1 ml of tetrahydrofuran/methanol 1:1 is added with stirring at ice bath temperature to 37 mg of (6-amino-2,3-dioxo-1,2,3,4-tetrahydrobenzo[f]quinoxalin-4-yl)-methanephosphonic acid diethyl ester in 2 ml of tetrahydrofuran z.A., to which 13 mg of sodium borohydride was added. Then, another 10 mg of sodium boronate is added and worked up for 1 more hour. The mixture is neutralized and extracted with ethyl acetate. After chromatography with a little silica gel, 16 mg of product is obtained.

After saponification of the ester, there is obtained
[6-(Piperidin-1-yl)-2,3-dioxo-1,2,3,4-tetrahydrobenzo[f] quinoxalin-4-yl]-methanephosphonic acid.
Synthesized analogously are:
[6-(Piperidin-1-yl)-2,3-dioxo-1,2,3,4-tetrahydrobenzo[f] quinoxalin-1-yl]-methanephosphonic acid diethyl ester as well as
[6-(piperidin-1-yl)-2,3-dioxo-1,2,3,4-tetrahydrobenzo[f] quinoxalin-1-yl]-methanephosphonic acid.

EXAMPLE 21

[6-(Morpholin-1-yl)-2,3-dioxo-1,2,3,4-tetrahydrobenzo[f]quinoxalin-4-yl]-methanephosphonic acid

[6-(Morpholin-1-yl)-2,3-dioxo-1,2,3,4-tetrahydrobenzo [f]quinoxalin-4-yl]-methanephosphonic acid diethyl ester is obtained from (6-amino-2,3-dioxo-1,2,3,4-tetrahydrobenzo [f]quinoxalin-4-yl)-methanephosphonic acid diethyl ester according to the method by reaction with 3-oxa-glutaric acid dialdehyde that is described in Example 20. With the usual method, there is obtained

[6-(Morpholin-1-yl)-2,3-dioxo-1,2,3,4-tetrahydrobenzo [f]quinoxalin-4-yl]-methanephosphonic acid.

Obtained analogously are:

[6-(Morpholin-1-yl)-2,3-dioxo-1,2,3,4-tetrahydrobenzo[f]quinoxalin-1-yl]-methanephosphonic acid diethyl ester as well as

[6-(Morpholin-1-yl)-2,3-dioxo-1,2,3,4-tetrahydrobenzo[f]quinoxalin-1-yl]-methanephosphonic acid and 1-[6-(morpholin-1-yl)-2,3-dioxo-1,2,3,4-tetrahydrobenzo[f]quinoxalin-1-yl]-ethanephosphonic acid diethyl ester as well as 1-[6-(morpholin-1-yl)-2,3-dioxo-1,2,3,4-tetrahydrobenzo[f]quinoxalin-1-yl]-ethanephosphonic acid.

EXAMPLE 22

1-[6-(Imidazolyl)-2,3-dioxo-1,2,3,4-tetrahydrobenzo[f]quinoxalin-1-yl]-ethanephosphonic acid diethyl ester or 1-[6-(imidazolyl)-2,3-dioxo-1,2,3,4-tetrahydrobenzo[f]quinoxalin-1-yl]-ethanephosphonic acid are produced by nucleophilic aromatic substitution from the halogen derivatives with imidazole as nucleophile.

Also, there are produced

[6-(Imidazolyl)-2,3-dioxo-1,2,3,4-tetrahydrobenzo[f]quinoxalin-1-yl]-methanephosphonic acid diethyl ester

[6-(imidazolyl)-2,3-dioxo-1,2,3,4-tetrahydrobenzo[f]quinoxalin-1-yl]-methanephosphonic acid

[6-(imidazolyl)-2,3-dioxo-1,2,3,4-tetrahydrobenzo[f]quinoxalin-4-yl]-methanephosphonic acid diethyl ester

[6-(imidazolyl)-2,3-dioxo-1,2,3,4-tetrahydrobenzo[f]quinoxalin-4-yl]-methanephosphonic acid.

We claim:

1. A benzo[f]quinoxalinedione compound of formula I

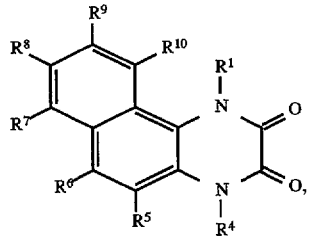

in which $R^1$ and $R^4$ are the same or different and mean hydrogen, $C_{1-12}$ alkyl substituted with $R^2$, $C_{2-12}$ alkenyl substituted with $R^2$, $C_{2-12}$ alkynyl substituted with $R^2$, $C_{3-7}$ cycloalkyl substituted with $R^2$, —$(CH_2)_n$—$C_{6-12}$ aryl, which is substituted with $R^2$ in the aryl or in the alkyl radical or —$(CH_2)_n$-hetaryl, which is substituted with $R^2$ in the hetaryl or alkyl radical, and $R^1$ and $R^4$ do not mean hydrogen at the same time, $R^5$, $R^6$, $R^7$, $R^8$, $R^9$ and $R^{10}$ are the same or different and mean hydrogen, halogen, nitro, $NR^{16}R^{17}$, $NHCOR^{11}$, $SO_{0-3}R^{12}$, $C_{3-7}$ cycloalkyloxy, $COR^{13}$, cyano, $CF_3$, $OCH_2CF_3$, $C_{1-6}$ alkyl or $C_{1-6}$ alkoxy, and $R^2$ is —CN, -tetrazole, —C(NOH)NH2, —CO—$R^3$ or —PO—XY and $R^2$ is the same or different in one to two places, and n is 0, 1, 2, 3, 4 or 5, $R^3$ means hydroxy, $C_{1-6}$ alkoxy or $NR^{14}R^{15}$, X and Y are the same or different and mean hydroxy, $C_{1-6}$ alkoxy, —O—$(CH_2)_p$—O—, $C_{1-4}$ alkyl or $NR^{14}R^{15}$ and p is 1, 2 or 3 and $R^{11}$ means $C_{1-6}$ alkyl or phenyl, which can be substituted with halogen, $R^{12}$ means hydrogen, $C_{1-4}$ alkyl, $NH_2$, $N(C_{1-4}$ alkyl$)_2$, —$NH(C_{1-4}$ alkyl$)$, —$NH$—$CH_2CONH_2$, —$CH_2CONH_2$, $CF_3$ or —$NH$—$(CH_2)_n$—$R^2$ and $R^{13}$ means hydroxy, $C_{1-6}$ alkoxy, $C_{1-6}$ alkyl or $NR^{14}R^{15}$, $R^{14}$ and $R^{15}$, $R^{16}$ and $R^{17}$ are the same or different and mean hydrogen, —CO—$C_{1-6}$ alkyl, phenyl or $C_{1-6}$ alkyl, which can be optionally substituted with $C_{1-4}$ alkoxy or with an amino group optionally mono- or disubstituted with $C_{1-4}$ alkyl or together with the nitrogen atom can form a 5- to 7-membered saturated heterocycle, which can contain another N, S or O atom and can be substituted or can form an unsaturated 5-membered heterocycle, which can contain 1–3N atoms and can be substituted, as well as their isomers or salts, and, if $R^5$–$R^{10}$ is hydrogen, $R^1$ or $R^4$ does not mean methanephosphonic acid or ethane-1-phosphonic acid.

2. (6-Nitro-2,3-dioxo-1,2,3,4-tetrahydrobenzo[f]quinoxalin-1-yl)-methanephosphonic acid (6-nitro-7-sulfamoyl-2,3-dioxo-1,2,3,4-tetrahydrobenzo[f]quinoxalin-1-yl)-methanephosphonic acid (6-nitro-7-sulfonamido-2,3-dioxo-1,2,3,4-tetrahydrobenzo[f]quinoxalin-4-yl)-methanephosphonic acid (6-nitro-8-sulfonamido-2,3-dioxo-1,2,3,4-tetrahydrobenzo[f]quinoxalin-1-yl)-methanephosphonic acid (6-nitro-8-sulfonamido-2,3-dioxo-1,2,3,4-tetrahydrobenzo[f]quinoxalin-4-yl)-methanephosphonic acid (6-nitro-8,10-disulfonamido-2,3-dioxo-1,2,3,4-tetrahydrobenzo[f]quinoxalin-1-yl)-methanephosphonic acid (6-nitro-8,10-disulfonamido-2,3-dioxo-1,2,3,4-tetrahydrobenzo[f]quinoxalin-4-yl)-methanephosphonic acid (6-nitro-2,3-dioxo-1,2,3,4-tetrahydrobenzo[f]quinoxalin-1-yl)-methanecarboxylic acid (6-nitro-7-sulfamoyl-2,3-dioxo-1,2,3,4-tetrahydrobenzo[f]quinoxalin-1-yl)-methanecarboxylic acid (6-nitro-2,3-dioxo-1,2,3,4-tetrahydrobenzo[f]quinoxalin-yl)-methanecarboxylic acid 1-(6-nitro-2,3-dioxo-1,2,3,4-tetrahydrobenzo[f]quinoxalin-1-yl)-ethane-1-carboxylic acid 1-(6-nitro-7-sulfamoyl-2,3-dioxo-1,2,3,4-tetrahydrobenzo[f]quinoxalin-1-yl)-ethane-1-carboxylic acid 1-(6-nitro-2,3-dioxo-1,2,3,4-tetrahydrobenzo[f]quinoxalin-yl)-ethane-1-carboxylic acid (6-nitro-2,3-dioxo-1,2,3,4-tetrahydrobenzo[f]quinoxalin-yl)-methanephosphonic acid.

3. A method for treatment of a disease caused by hyperactivity of excitatory amino acids which comprises administering an effective amount of a compound according to claim 1.

4. A process for the production of a compound of formula I according to claim 1, which comprises:

a) cyclizing a compound of formula II or III

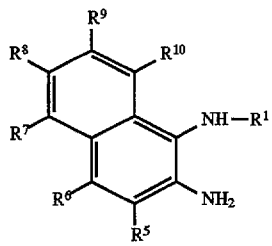
(II)

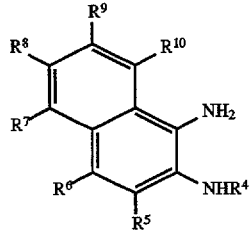
(III)

with oxalic acid or a reactive oxalic acid derivative or b) reacting a compound of formula IV or V

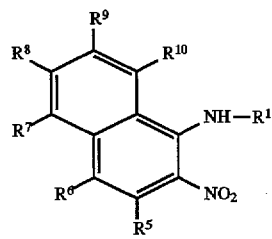
(IV)

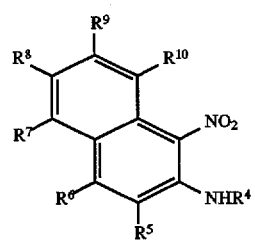
(V)

with oxalic acid or a reactive oxalic acid derivative and after reduction of the nitro group cyclizing the resultant compound or c) reacting a compound of formula VI

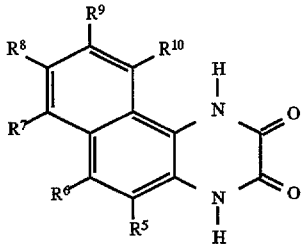
(VI)

in the presence of a base, with $R^1$ Z or $R^4$ Z, in which Z represents a leaving group, and then optionally saponifying the ester group or esterifying or amidating the acid group or reducing the nitro group to the amino group or alkylating or acylating the amino group or exchanging the amino group for halogen or cyano or introducing a nitro group or halogen or converting or nucleophilically substituting a nitrile into the tetrazole or amidoxime or separating the isomers or forming the salts.

5. A pharmaceutical composition comprising a pharmaceutically effective amount of a compound according to claim 1.

6. A compound according to claim 1, wherein $R^2$ is —$COR^3$ or —PO-XY and one or both of $R^1$ and $R^4$ are alkyl substituted with $R^2$.

7. The method of claim 3, wherein the compound is administered in a daily dose of 5 to 200 mg.

8. The method of claim 3, wherein the disease is a neurodegenerative disorder, postischemic cell destruction, cell destruction after cerebral trauma, senile dementia, multi-infarct dementia, epilepsy or muscle spasms.

9. The method of claim 3, wherein the disease is anxiety, schizophrenia, migraine, pain, a sleep disorder or drug withdrawal.

10. The method of claim 3, wherein the compound is administered in a daily dose of 0.5 to 1000 mg.

* * * * *